(12) United States Patent
Virtanen

(10) Patent No.: US 11,054,406 B2
(45) Date of Patent: Jul. 6, 2021

(54) ANALYZING FAULT GAS CONCENTRATION IN LIQUID

(71) Applicant: Vaisala Oyj, Vantaa (FI)

(72) Inventor: Sami Virtanen, Helsinki (FI)

(73) Assignee: Vaisala Oyj, Vantaa (FI)

( * ) Notice: Subject to any disclaimer, the term of this patent is extended or adjusted under 35 U.S.C. 154(b) by 496 days.

(21) Appl. No.: 16/061,371

(22) PCT Filed: Aug. 18, 2017

(86) PCT No.: PCT/FI2017/050581
§ 371 (c)(1),
(2) Date: Jun. 12, 2018

(87) PCT Pub. No.: WO2019/034802
PCT Pub. Date: Feb. 21, 2019

(65) Prior Publication Data
US 2020/0333317 A1    Oct. 22, 2020

(51) Int. Cl.
*G01N 33/28* (2006.01)
*G01N 33/00* (2006.01)

(52) U.S. Cl.
CPC ..... *G01N 33/2841* (2013.01); *G01N 33/0016* (2013.01); *G01N 33/0059* (2013.01)

(58) Field of Classification Search
CPC .......... G01N 33/2841; G01N 33/0016; G01N 33/0069
USPC ....... 73/23.2, 1.02, 1.06, 19.1, 23.21, 31.04, 73/31.05; 338/34, 35; 356/436, 437; 324/601, 658, 691, 663, 664, 693–701; 361/279, 286; 250/343
See application file for complete search history.

(56) References Cited

U.S. PATENT DOCUMENTS

| | | | |
|---|---|---|---|
| 5,659,126 | A | 8/1997 | Farber |
| 8,265,881 | B1 | 9/2012 | Lakhotia et al. |
| 2015/0053861 | A1 | 2/2015 | Wong et al. |
| 2016/0116451 | A1 | 4/2016 | Mahoney et al. |
| 2016/0231303 | A1 | 8/2016 | Park et al. |

FOREIGN PATENT DOCUMENTS

| | | |
|---|---|---|
| CN | 101363813 A | 2/2009 |
| CN | 204085942 U | 1/2015 |

*Primary Examiner* — Robert R Raevis
(74) *Attorney, Agent, or Firm* — Laine IP Oy

(57) ABSTRACT

According to an example aspect of the present invention, there is provided analyzing fault gas concentrations in a liquid. Concentration of at least one dissolved fault gas in the liquid is measured at least at two temperatures. Disturbing gas contribution is determined in at least one temperature on the basis of the fault gas concentration measurements. Fault gas concentrations are analyzed by compensating fault gas concentrations on the basis of the determined disturbing gas contribution.

14 Claims, 3 Drawing Sheets

ANALYZING FAULT GAS CONCENTRATION IN LIQUID

FIELD

The present invention relates to analyzing fault gas concentrations in a liquid.

BACKGROUND

Analysis of gases dissolved in liquids is a common technological challenge in monitoring the gas content, for example of oil and water, in industrial and environmental applications. An important example is the condition monitoring of large electrical power transformers, which is mainly based on transformer oil dissolved gas analysis.

Electrical power transformers are known to degrade and fail due to aging, thermal, mechanical and electrical stresses. When electrical power transformers degrade and create failure mechanisms, their insulation material—oil and cellulose—breaks down and generates certain gases commonly referred to as "fault gases" which are dissolved in the oil. Such fault gases may include hydrogen ($H_2$), carbon monoxide (CO), carbon dioxide ($CO_2$), methane ($CH_4$), acetylene ($C_2H_2$), ethylene ($C_2H_4$), and ethane ($C_2H_6$). It is well known in the transformer industry that the amount and nature of fault gases and their rates of change can be used to determine the condition and the type and severity of faults in transformers. For example, hydrogen is often associated with low energy electrical discharge (corona) while acetylene is related to high energy arcing (IEEE Std C57.104—Guide for the Interpretation of Gases generated in oil-immersed transformers).

Online dissolved gas analysis (DGA) devices are used for continuous monitoring of oil-filled high-voltage transformers and switchgear. They typically determine concentrations of hydrogen, water, lightest hydrocarbons such as methane, ethane, ethylene and acetylene, and carbon oxides such as carbon monoxide and carbon dioxide, dissolved in insulating oils. From these so-called fault gas concentrations and their rates of changes, one can infer much about the condition of the monitored device and the possible fault mechanisms it has.

In addition to the above-mentioned fault gases, used transformer oils contain a multitude of other chemical compounds that partially vaporize as gases are extracted from the oil for the measurement. These disturbing gases often have higher concentrations than the fault gases, and thus their adverse effect on the measurement accuracy of the latter can be substantial.

US2016116451A1 discloses a gas monitoring apparatus having thermal conditioning zones for oil to provide an environment in which variations in oil temperature and ambient temperature are eliminated to insure that analytical data are not affected by the environmental conditions. Oil samples are thermally conditioned to a pre-set temperature. A primary fluid path is used to deliver oil from the utility asset to standard analysis and a secondary fluid path is provided for calibration purposes. In the secondary fluid path the oil is exposed to air or calibration gas allowing the oil to equilibrate with the air or calibration gas. When the calibration is called for, the oil from the secondary fluid path is introduced to the sensor.

US2015053861A1 discloses circulating transformer oil through an NDIR gas sensor system which obtains an acetylene concentration by calculating a detected acetylene concentration obtained by an absorption biased ("AB") NDIR acetylene gas sensor, calculating a detected carbon dioxide concentration obtained by an AB NDIR carbon dioxide gas sensor, calculating a detected water vapor concentration obtained by an AB NDIR water vapor NDIR gas sensor and then determining the acetylene concentration from the detected acetylene concentration through use of the detected carbon dioxide and water vapor concentrations to compensate for their interference.

US2016231303A1 discloses measuring hydrogen gas dissolved in liquid. A reference electrode is isolated from the liquid and the hydrogen gas in a sealing space. The reference electrode is thus in communication with the external air through the reference gas passage.

Analysis of gases dissolved in liquid is particularly challenging, when temperature of the liquid varies and only a portion of the dissolved gases can be calibrated in the analyzer device. Because solubility of gases in liquids depends on temperature, one typically aims at thermalizing the analyzed liquid samples to have the same, constant temperature.

SUMMARY OF THE INVENTION

The invention is defined by the features of the independent claims. Some specific embodiments are defined in the dependent claims.

According to a first aspect of the present invention, there is provided a method for analyzing fault gas concentrations in a liquid, the method comprising:

measuring, by a liquid analyzer comprising a system for sampling gas from the liquid and an analyzer for gas sampled by the system, concentration of at least one dissolved fault gas in the liquid at least at two temperatures;

determining, by the liquid analyzer, a disturbing gas contribution in at least one temperature on the basis of the fault gas concentration measurements; and analyzing, by the liquid analyzer, fault gas concentrations by compensating fault gas concentrations on the basis of the determined disturbing gas contribution.

According to a second aspect of the present invention, there is provided a liquid analyzer comprising a system for sampling gas from a liquid and an analyzer for gas sampled by the system, wherein the liquid analyzer is caused to:

measure concentration of at least one dissolved fault gas in the liquid at least at two temperatures;

determine a disturbing gas contribution in at least one temperature on the basis of the fault gas concentration measurements; and analyze fault gas concentrations by compensating fault gas concentrations on the basis of the determined disturbing gas contribution.

According to a third aspect of the present invention, there is provided a computer program product comprising instructions to cause a liquid analyzer comprising a system for sampling gas from the liquid and an analyzer for gas sampled by the system, to execute a method according to an aspect.

EMBODIMENTS

Figure 1:
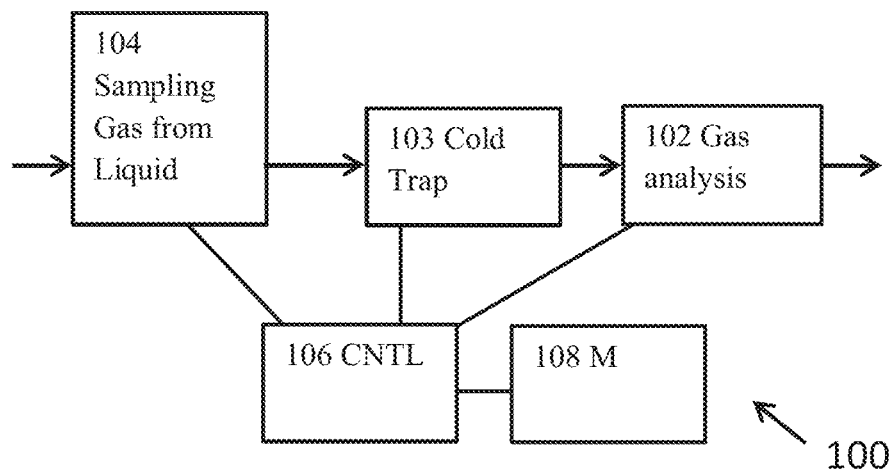
FIG. 1 illustrates a schematic view of liquid analyzer in accordance with at least some embodiments.

FIG. 1 illustrates a schematic view of liquid analyzer in accordance with at least some embodiments. A liquid analyzer 100, 110 comprises a system 104 for sampling gas from the liquid and an analyzer 102 for gas sampled by the system. Lines with arrow heads in FIG. 1 illustrate flow of gas and liquid, whereas lines without arrow heads illustrate connections for control and data communications. The liquid analyzer may be at least caused to: measure concentration of at least one dissolved fault gas in the liquid at least at two temperatures, determine a disturbing gas contribution in at least one temperature on the basis of the fault gas concentration measurements, and analyze fault gas concentrations by compensating fault gas concentrations on the basis of the determined disturbing gas contribution. In this way effects of disturbing gases on dissolved fault gas analysis may be considerably reduced.

The gas sampling system, i.e. the system 104 for sampling gas from the liquid, may be capable of receiving liquid, e.g. a liquid sample, from a liquid source and extracting a gas sample from the received liquid sample. In an example, the gas sampling system may be connected to the liquid source by input piping that may be controlled by opening and closing valves such that liquid samples may be received to the gas sampling system 104. The gas sample may be extracted from the liquid using a vacuum extraction method or a head-space sampling method, for example.

The liquid may comprise dissolved gases that may indicate a one or more faults in the liquid source and/or the system comprising the liquid source. The dissolved gases indicating faults may be referred to as fault gases. The liquid analyzer may be used for measuring concentration of at least one dissolved fault gas in the liquid, whereby results of the concentration measurements provided by the liquid analyzer may be utilized in condition monitoring of the liquid and the system comprising the liquid source. However, in addition to the fault gases, the dissolved gases in the liquid may comprise disturbing gases, which do not serve for detecting faults and/or which distort concentration measurements of the fault gases by the liquid analyzer. In practice the disturbing gases may comprise all other gases that are dissolved in the liquid by amounts that are significant to results of the fault gas concentration measurement. The concentrations of fault gases and disturbing gases in the extracted gas samples may behave differently, when temperature of the liquid varies, since the fault gases and the disturbing gases may have differences in the temperature dependency of gas dissolution coefficients known as Ostwald's coefficients. Therefore, relative amount of the fault gases and the disturbing gases in the extracted gas samples may vary from one temperature to another. Particularly, the temperature dependence of the solubility of the disturbing gases may be stronger than the temperature dependence of the solubility of the fault gases.

Examples of liquid sources comprise liquid reservoirs. A liquid reservoir may be provided in an electrical asset examples of which comprise switchgear and electric power transformers, in which electrical parts are immersed in transformer oil. The fault gases may comprise at least one of hydrogen, water, methane, ethane, ethylene, acetylene, carbon monoxide and carbon dioxide. In high voltage applications, the disturbing gases may comprise somewhat heavier hydrocarbons than the fault gases and other compounds like light alcohols, ketones and aldehydes, or hydrocarbons containing at least 3 carbon atoms per molecule. For majority of these disturbing gases, the temperature dependence of solubility in transformer oils is considerably stronger than for above-mentioned fault gases, and such that concentrations of these compounds in the extracted gas increase strongly with increasing extraction temperatures, and vice versa.

The gas analyzer 102, may be capable of measuring a concentration of one or more fault gases in a gas sample extracted by the gas sampling system. The concentration of the fault gases in a gas sample may be measured by the gas analyzer based on NDIR absorption or photoacoustic spectroscopy (PAS) technologies, for example. Fault gas concentrations may be calculated from the NDIR absorption spectra or from the PAS acoustic power spectrum resulting from measurements performed by the gas analyzer. In NDIR absorption measurements, according to Beer's law $I(\lambda)/I_0(\lambda) = \exp[-\Sigma_n A_n(\lambda)Lc_n]$, where $I(\lambda)$ is the transmitted intensity at wavelength $\lambda$ in the presense of gases and $I_0(\lambda)$ without them, $A_n(\lambda)$ are absorption coefficients specific to each gas, L is the optical path length, $c_n$ are concentrations of gases and the sum goes over all absorbing gases present in the measurement. The relative absorption $I(\lambda)/I_0(\lambda)$ can be linearized with respect to contributions of individual gases: $S(\lambda) = -\log[I(\lambda)/I_0(\lambda)] = \Sigma_n A_n(\lambda)Lc_n$ is the linearized relative absorption. It is to be noted that the gas analyzer is not restricted to NDIR absorption or photoacoustic measurement technologies and the gas analyzer may be implemented to utilize other measurement technologies.

The fault gases comprise at least one of hydrogen, water, methane, ethane, ethylene, acetylene, carbon monoxide and carbon dioxide. Concentration of fault gases may be measured for condition monitoring of the liquid source and/or the system comprising the liquid source. The condition monitoring may be performed continuously such that faults and/or aging indicated by results of the fault gas concentration measurements may be detected and appropriate action may be taken.

The extraction of gas samples may be temperature sensitive because of temperature dependence of the gas dissolution coefficients, known as Ostwald's coefficients, which determine equilibrium concentration ratios of various compounds in liquid and gas phases. An extracted liquid sample may comprise a mixture of dissolved gases comprising both fault gases and disturbing gases. Measurements by the gas analyzer based on NDIR absorption provide the linearized relative absorption S for a gas sample extracted from the liquid sample at temperature T. The relative absorption may be measured at wavelengths $\lambda$, such that the linearized relative absorption becomes $S(\lambda, T)$. The relative absorption can be written according to the following formula (1):

$$S(\lambda,T) = Sf(\lambda,T) + Sd(\lambda,T), \quad (1)$$

where $S(\lambda,T)$ is the linearized relative absorption for gas extracted from a liquid sample at temperature T, $\lambda$ is the wavelength of the infrared radiation passing through the gas volume and detected by the gas analyzer based on NDIR absorption measurement technology, Sf is the absorption contribution due to fault gases and Sd is the disturbing gas contribution for a given $\lambda$ and T. Sd is the part that causes distortion to the fault gas measurement results.

It should be appreciated that measurements by a gas analyzer based on PAS technology provide an acoustic power spectrum for a gas sample extracted from the liquid sample at temperature T and the linearized acoustic power spectrum can be divided to fault gas and disturbing gas contributions similarly as in formula (1).

However, dissolution coefficients and consequently extraction of the disturbing gases may be more dependent on the temperature than the dissolution coefficients and extraction of the fault gases, essentially since molecules of the disturbing gases may be heavier than those of the fault gases. Consequently, with increasing extraction temperature disturbing gas contribution to fault gas measurements tends to rise rapidly. On the other hand, at low extraction temperatures, disturbing gas contribution is relatively much smaller.

The gas sampling may be performed at two or more temperatures within a temperature range of at least part of the gas sampling system 104. Accordingly, the gas sampling system is capable of extracting samples of dissolved gas from the liquid samples at temperatures that may be referred to as extraction temperatures or gas sampling temperatures. The temperatures of the temperature range for gas sampling may be achieved by active heating, active cooling and/or changes of ambient temperature of the liquid analyzer. For example, the gas sampling system or the at least part of the gas sampling system may be capable of heating and/or cooling the liquid samples to one, two or more temperatures for extracting samples of dissolved gas from the liquid samples. Active heating may be achieved by a heating element in the gas sampling system 104. Active cooling may be achieved by a cooling element in the gas sampling system 104. In this way gas samples may be extracted in the temperatures within the temperature range for gas concentration measurements by the gas analyzer.

In an embodiment, at least part of the fault gas measurements may be performed in a time interval wherein there is a local minimum in ambient temperature. In this way the liquid or gas sample obtained from the liquid may be thermalized to the local minimum, or at least close to the local minimum, in the ambient temperature, and the effect of the disturbing gases to the fault gas measurements may be kept small even when active cooling is not available. Furthermore, it should be appreciated that instead of active heating and/or active cooling of the liquid samples, the liquid samples may be brought into two or more temperatures, including temperatures near a local minimum ambient temperature, by changes in the ambient temperature of the liquid source and/or the liquid analyzer. Changes in the ambient temperature may be caused by temperature variations between times of day and/or changes in weather conditions.

The gas analyzer 102 may be provided with an output for removing gas after a measurement of fault gas concentrations has been performed. Preferably, the gas from the gas analyzer is dissolved back into the liquid sample obtained from the liquid source such that the analyzer will not gradually affect the gas concentrations of the liquid source. The gas sampling system 104 may be capable of dissolving the gas from the gas analyzer 102 back into the liquid sample. After the gas is dissolved back into the liquid sample, the liquid sample may be returned back into the liquid source by the gas sampling system 104.

In an embodiment, the liquid analyzer comprises a cold trap 103. The cold trap may provide at least partial filtering, prior to the fault gas concentration analysis, for the disturbing gases in the gas sample. The filtering is based on at least locally cooling down the sampled gas to a filtering temperature. In this way the disturbing gas contribution in the gas sample fed to the gas analyzer may be reduced and accuracy of the fault gas concentration measurement may be improved. The cold trap may be positioned in the liquid analyzer such that gas extracted by the gas sampling system 104 may be fed to the gas analyzer 102 via the cold trap. The cold trap may be controlled to cool down the sampled gas to a lower temperature than the extraction temperature. The effect of the cold trap to fault gas concentrations may be insignificant or very small due to higher vapor pressures of the fault gases at the cold trap operating temperatures.

In an embodiment, the cold trap may be capable of being operated in one or more filtering temperatures. The gas samples filtered by the cold trap provide improved accuracy for measuring fault gas concentrations and subsequently determining disturbing gas contributions. In order to facilitate self-cleaning of the cold trap and to extend its lifetime, it is preferable to cool the cold trap only when needed to determine the disturbing gas contributions. Using the cold trap without cooling the sampled gas, or even by heating it, the cold trap may be effectively cleaned from residues left from cooling the sampled gas.

In an embodiment, the liquid analyzer may comprise a controller 106 operatively connected to the gas sampling system 104, the gas analyzer 102, and the cold trap 103 for analyzing fault gas concentrations in a liquid. The controller may be connected to a memory 108 storing computer readable instructions, computer program code or computer program product comprising instructions that when executed by the controller may cause one or more functionalities described in an embodiment described herein. Connections between the controller, gas analyzer, gas sampling system, cold trap and memory may be capable of communications of control information and/or data. The connections may be implemented by electrical connections, for example by electrical wiring and data buses. Examples of the controller comprise a computer, a processor and a data processing device.

In an embodiment, the liquid analyzer 100 is a hermetical system. Accordingly, liquid and gas within the liquid analyzer may be prevented from escaping the liquid analyzer and ambient air may be prevented from entering the liquid analyzer. In this way fault gas concentration measurements and the liquid to be analyzed may be unaffected by ambient air.

Figure 2:
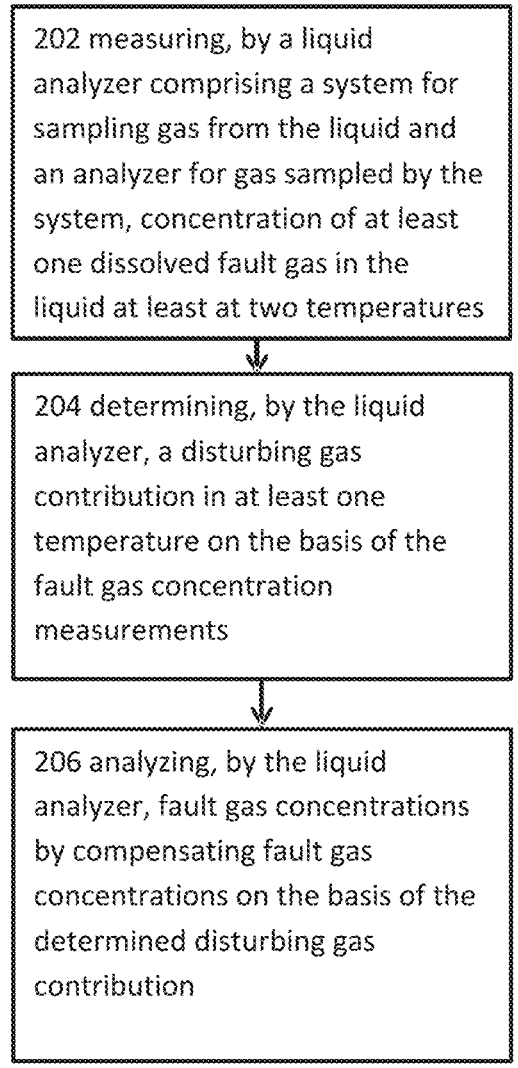
FIG. 2 illustrates a method for analyzing fault gas concentrations in accordance with at least some embodiments.

FIG. 2 illustrates a method for analyzing fault gas concentrations. The method may be performed by a liquid analyzer described with reference to FIG. 1. The method enables reducing effects of disturbing gases on dissolved fault gas analysis.

Phase 202 comprises measuring, by a liquid analyzer comprising a system for sampling gas from the liquid and an analyzer for gas sampled by the system, concentration of at least one dissolved fault gas in the liquid at least at two temperatures T. The measured fault gas concentrations may indicate concentrations of one or more fault gases.

Phase 204 comprises determining, by the liquid analyzer, a disturbing gas contribution in at least one temperature on the basis of the fault gas concentration measurements results of phase 202. Since the fault gases and the disturbing gases may have differences in the temperature dependency of gas dissolution coefficients known as Ostwald's coefficients, their concentrations in the liquid and the extracted gas may behave differently depending on the temperature of the liquid. The temperature dependence of dissolution coefficients of the fault gases and the temperature dependence of dissolution coefficients of the disturbing gases may be different. Utilizing the different temperature dependencies of solubilities of the fault gases and the disturbing gases, it is possible to determine disturbing gas contributions sufficiently reliably at one or more temperatures such that accuracy of the fault gas concentration analysis may be improved.

Phase 206 comprises analyzing, by the liquid analyzer, fault gas concentrations by compensating fault gas concentrations on the basis of the determined disturbing gas contribution. In this way the effect of disturbing gases to the analysis of the fault gas concentrations may be reduced when the liquid analyzer is used for example to condition monitoring based on the detected fault gas concentrations. If using NDIR absorption measurement principle, the compensation may be performed by subtracting the disturbing gas contribution at that temperature from the measured linearized total absorption spectrum to obtain the estimate for the contribution of the fault gases to the absorption—analogously for other measurement technologies. It should be appreciated that the phase 206 may be performed in a normal operation phase of the liquid analyzer, after at least one disturbing gas contribution has been determined in phase 204.

It should be appreciated that phases 202, 204 and 206 may be repeated separately or combined and they may be executed in a different order. After one of the phases has been executed once, information provided by the phase may be utilized in the other phases at least once and even repeatedly.

It is to be noted that preferably the measurements in phase 202 should be performed within time interval during which gas concentrations in the liquid remain essentially constant. One may relax this requirement at least to some degree by performing the measurements in a symmetrical and/or cyclical order with respect to temperature to reduce the effects of changes in gas concentrations in the liquid during the measurements. All or at least part of the measurement results corresponding to a certain temperature may then be averaged in order to further reduce the effects of gas concentration changes. The measurement order may be chosen such that to at least first order accuracy, the effect to the results of changes in the gas concentrations in the liquid during the measurements at least at two temperatures are cancelled. For example, for temperatures T1>T2>T3>T4, in a cyclical order for the measurements one may follow a sequence T1→T2→T3→T4→T3→T2→T1 in extraction temperature, and in a symmetrical order for the measurements, one may follow a sequence T1→T4→T2→T3 or T1→T4→T3→T2 or variations of these in extraction temperature. The results corresponding to temperatures T1, T2 and T3 above in the cyclical order may be averaged, for example. Accordingly, in the symmetrical order, the order of the measurements may be symmetrical around a center of the temperatures. In the cyclical order the measurements are performed at increasing order of temperatures to a highest temperature and then in a decreasing order of temperatures to the lowest temperature, or vice versa. In an example, the temperatures for the measurements may be evenly separated from each other: Tn=T1+(n−1)*ΔT. It should be appreciated that equal spacing may be applied between the temperatures or the spacing may be different, e.g. lower or higher between parts of the temperature range of the measurements. Measurements may be performed in both a symmetrical and in a cyclical order with respect to temperature. In an example, the measurements may be performed in both a symmetrical and in a cyclical order, when ordering of the measurements is changed over time from cyclical to symmetrical or vice versa. In a further example, a combination of both symmetrical and cyclical ordering of the measurements may be performed by applying the cyclical ordering at least in part in a different temperature range than a temperature range, where the symmetrical ordering is applied. By ordering of the measurements and further averaging the results, the majority of the adverse biasing effects due to gas concentration changes in the liquid during self-calibration can be eliminated.

It is also to be noted that various factors including but not limited to the extraction temperature and gas concentrations in the liquid may affect the disturbing gas contribution. If for example the gas measurement pressure changes considerably, it is preferable to determine the disturbing gas contribution anew.

In an embodiment, the fault gas concentrations may be measured in phase 202 at least at a temperature, where the disturbing gas contribution to fault gas concentration measurement results is low such that the results of fault gas concentration measurement may be used as an estimate of the actual fault gas concentrations in the liquid. Advantageously, one may use all the fault gas measurement results obtained in phase 202 to infer the temperature dependence of these results, and possibly extrapolate the results farther to the temperature region where disturbing gas contribution is expected to be smaller. Using such a method, one can improve the accuracy of the estimate $Sf,est(\lambda,T)$ to the actual fault gas contribution in the gas measurement for low temperatures T. Estimate of fault gas contribution $Sf,est(\lambda,T)$ for higher temperatures may then be computed based on the estimate of the actual fault gas concentrations in the liquid, the calibrated fault gas absorption spectra and the temperature dependence of the dissolution coefficients of the fault gases. Consequently, an estimate of disturbing gas contribution may be determined by formula (2):

$$Sd,est(\lambda,T)=S(\lambda,T)-Sf,est(\lambda,T) \qquad (2),$$

where $Sf,est(\lambda,T)$ is the estimate of fault gas contribution, and $Sd,est(\lambda,T)$ is the estimate of disturbing gas contribution, at temperatures T corresponding to measurements in phase 202. Accordingly, the $Sd,est(\lambda,T)$ may be determined at the measurement temperatures used in phase 202 by using the estimates of fault gas contributions at those temperatures and the measured linearized total absorption or total photoacoustic spectrum obtained from the measurements at those temperatures. Furthermore, interpolation and/or extrapolation may be used to obtain $Sd,est(\lambda,T)$ in the whole temperature range covered in phase 202, or even somewhat outside that range.

It should be appreciated that phases 202, 204 and 206 may serve for calibrating the liquid analyzer such that results of fault gas concentration measurements may be compensated for the effect of the disturbing gases. In an example, the phases 202, 204 and 206 may be performed in a self-calibration phase of the liquid analyzer. Accordingly, the liquid analyzer may have a self-calibration phase in addition to a normal operation phase. In the normal operation phase, phase 202 may be performed during condition monitoring purposes. In the calibration phase, phase 202 may be performed separately from the normal operation phase. In this way the disturbing gas contribution may be determined in a relatively short time period apart from the normal operation phase. It is preferable to perform the first self-calibration soon after installing the analyzer to find out the initial disturbing gas contribution. During the first self-calibration, the temperature dependent disturbing gas contribution is not known, and accuracy of the measurement results may be compromised. However, in subsequent self-calibration phases one may utilize the results of the previous self-calibrations, and the temperature variations needed in step 202 can be performed without essentially compromising measurement accuracy. Thus, the self-calibration phase can be combined with normal operation phase, and the user can obtain high quality measurement results without interruption even during self-calibration phases. This is very important from the user point of view, because the self-calibration phase typically requires performing several measurements, and it would not be acceptable to have such delays in the condition monitoring of the analyzed device. It is to be also noted that the temperature variations of phase 202 do not have to be driven by active thermalizing control, but can be generated for example by ambient temperature changes for the analyzer during its normal operation.

In an embodiment, prior to the fault gas concentration analysis, disturbing gases may be filtered from the sampled gas by a cold trap arranged in the liquid analyzer. In this way at least a fraction of heavier gases in the gas sample may be condensed and removed from the gas sample before fault gas concentration of the gas sample is measured in phase 202. The cold trap may be specifically utilized to enhance the accuracy in determining the estimate for the actual, or reference fault gas concentrations, and consequently Sf,est. When using such approach, one can separately perform the measurements at various temperatures without using the cold trap to obtain $S(\lambda,T)$.

In an embodiment, phase 204 may comprise determining the disturbing gas contribution on the basis of fault gas concentrations measured from gas filtered by the cold trap operated in one or more filtering temperatures. The gas samples may be filtered by the cold trap for reducing the amount of disturbing gases from the sampled gas such that improved accuracy for measuring fault gas concentrations and subsequently determining disturbing gas contributions may be obtained. Measuring the fault gas concentrations in the cold trap temperatures enables using extrapolation towards lower temperatures technique also with respect to cold trap temperature in order to find out even more accurate estimate to the actual, or reference fault gas concentrations, and consequently Sf,est.

In an embodiment, phase 204 may comprise determining fault gas contribution in the gas measurements at one, two or more temperatures on the basis of the temperature dependence of the dissolution coefficients of the fault gases, the calibrated fault gas absorption spectra and the reference fault gas concentrations obtained in phase 202. The reference fault gas concentrations in the liquid may be determined on the basis of fault gas concentrations measured in phase 202 at a temperature that is one of the lowest temperature points of the temperature range for gas sampling. The temperature for determining the reference fault gas concentrations may be for example a minimum temperature of the temperature range. Accordingly, the temperature for determining the reference fault gas concentrations may be a temperature, where the disturbing gas contribution is low such that the results of the fault gas concentration measurement, corresponding to $S(\lambda,T)$, may be used to estimate the actual fault gas concentrations at one of the lowest temperature points of the temperature range, e.g. the minimum temperature of the temperature range, Sf,est≈S. However, since especially without active cooling methods it is often not possible to attain temperatures in which the disturbing gas contribution is relatively small enough, it is often preferable to determine the reference fault gas concentrations in the liquid by extrapolating the results obtained in phase 202 to lower temperatures.

Figure 3:
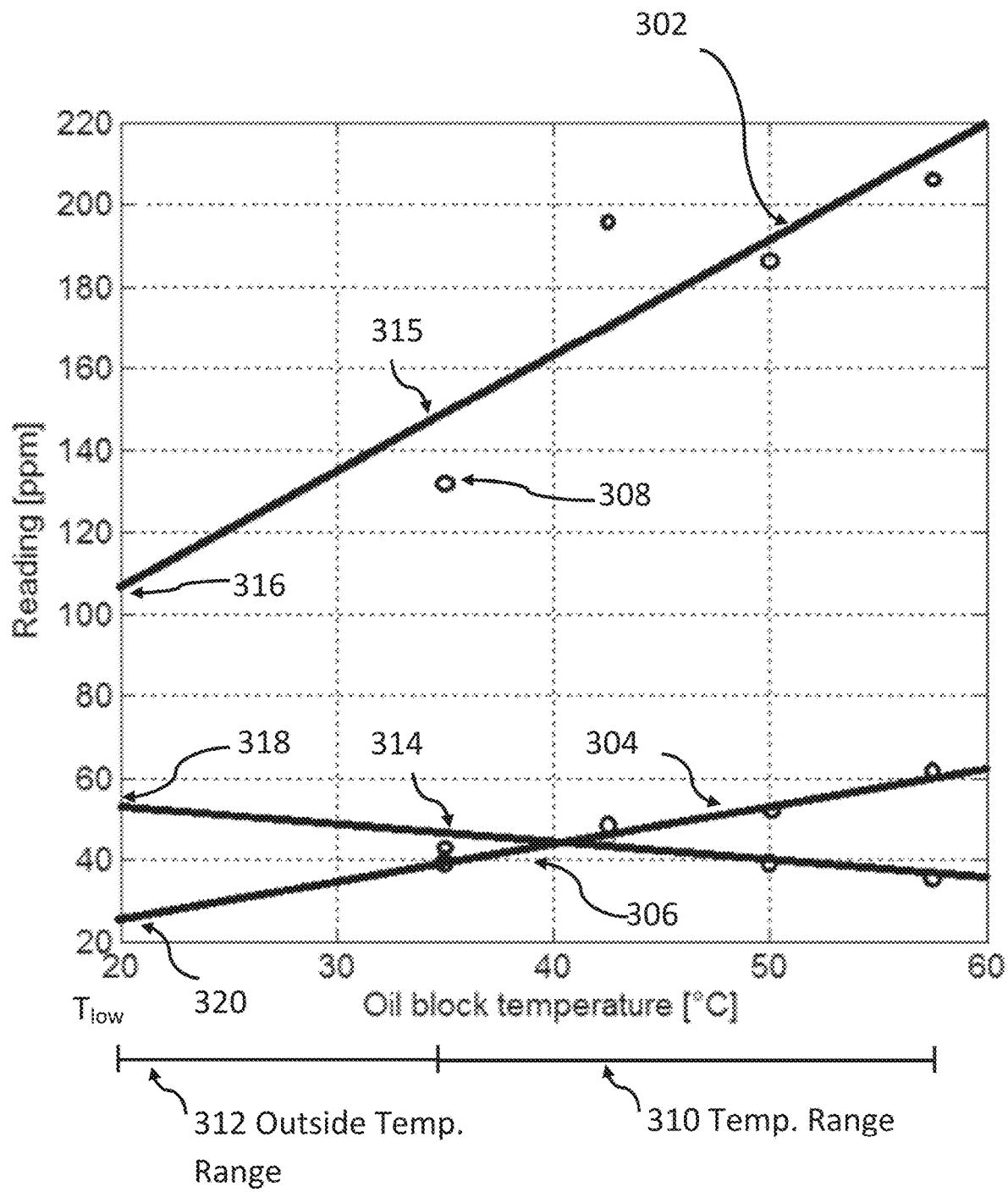
FIG. 3 illustrates results of fault gas concentration measurements in accordance with at least some embodiments.

FIG. 3 illustrates results of fault gas concentration measurements in accordance with at least some embodiments. The fault gas concentration measurements may have been performed by the liquid analyzer described with FIG. 1. The liquid analyzer may comprise a gas sampling system such that samples of dissolved gas may be extracted from the liquid samples at least at two temperatures that may be referred to as extraction temperatures. Results of the fault gas concentration measurements are illustrated by circles 308 at the extraction temperatures. The extraction temperatures may be within a temperature range 310. In FIG. 3 the illustrated example temperature range is from about 35° C. to 57° C. Results of the fault gas concentration measurements outside 312 of the temperature range 310 may be obtained by extrapolating the results of the fault gas concentration measurements using an extrapolation function. The extrapolation function may be determined on the basis of the convexity of the results 308. FIG. 3 illustrates an example, where results of the fault gas concentration measurements have been extrapolated down to temperature 20° C. by linear extrapolation functions 302, 304, 306 applied to results of concentration measurements of three different fault gases.

In an embodiment at least one reference fault gas concentration may be determined on the basis of a fault gas concentration in the liquid 314, 315 measured at one of the lowest temperature points of the temperature range 310, e.g. a minimum temperature of the temperature range 310, or values of fault gas concentrations 316, 318, 320 extrapolated to a lower temperature outside 312 of the temperature range 310. In this way estimates of the actual fault gas concentrations in the liquid may be obtained since the disturbing gas contribution $Sd(\lambda,T)$ is expected to be relatively smaller the lower the extraction temperature T is. Accordingly, at a sufficiently low extraction temperature $T_{low}$ the $Sd(\lambda,T)$ may be approximately omitted from the formula (1), whereby formula (1) becomes $Sf(\lambda, T_{low}) \approx S(\lambda, T_{low})$. Accordingly, $S(\lambda, T_{low})$ may be an estimate of the linearized absorption spectrum corresponding to fault gases at temperature $T_{low}$. Using fault gas concentration measurement results obtained by extrapolation or from the gas concentration measurement results at one of the lowest temperature points of the temperature range, the fault gas calibration spectra and their temperature dependent dissolution coefficients, the estimate of fault gas contribution $Sf,est(\lambda,T)$ may be computed for higher temperatures e.g. the temperatures outside 312 the temperature range and within the temperature range 310. Consequently, disturbing gas contribution may be determined by formula (2) at the temperatures outside 312 the temperature range and within the temperature range 310 of the fault gas concentration measurements in phase 202.

Using $Sf,est(\lambda,T)$ and linearized total absorptions $S(\lambda,T)$ corresponding to measurements of phase 202, one then obtains using equation (2) the estimate for disturbing gas contribution to the absorption at the temperatures corresponding to phase 202. Furthermore, utilizing interpolation and function fitting, $Sd,est(\lambda,T)$ may be defined for all temperatures of the temperature range 310. By extrapolation, the disturbing gas contribution estimate can be extended even somewhat outside of the temperature range 310. In this way, the disturbing gas contribution may be determined within the temperature range 310 and somewhat outside of it. This allows that the measurement accuracy is not compromised even if the extraction temperature varies for subsequent fault gas concentration measurements since estimated disturbing gas contribution may be subtracted from the total linearized absorption measured by the gas analyzer at various temperatures, whereby adverse contribution of disturbing gases to measurement accuracy can be substantially reduced.

Instead of computing Sd,est($\lambda$,T) and subtracting it from the total linearized absorption spectra corresponding to subsequent measurements, determination of the disturbing gas contribution and compensation of fault gas measurement results in phases 204 and 206 can be done alternatively in the following way: Based on measurement results obtained in phase 202, one determines the reference fault gas concentrations in the liquid as described above. Then offset corrections for the fault gas concentrations are computed as differences between the concentrations results in phase 202 measurements and the reference fault gas concentrations. This yields offset corrections for the fault gases at each temperature corresponding to phase 202 measurements. By using interpolation and/or extrapolation, the offset corrections can be computed also for other temperatures. Finally, in subsequent measurements, compensation of fault gas measurement results is done by subtracting the determined concentration offsets directly from the uncompensated concentration measurements result. This alternative method is simpler than the method based on explicitly computing the linearized disturbing gas contribution Sd,est($\lambda$,T), but it has inferior accuracy if the fault gas concentrations change after the self-calibration, because the effect of nonlinearities in the measurement are not taken properly into account. However, even this simpler method can be very effective in reducing the adverse effects of disturbing gases to the fault gas concentration measurement accuracy.

A computer program product comprising instructions to cause a liquid analyzer comprising a system for sampling gas from the liquid and an analyzer for gas sampled by the system, to execute a method or functionalities according an embodiment.

In an embodiment, there is provided a non-transitory computer readable medium having stored thereon a set of computer readable instructions that, when executed by at least one processor, cause a method or functionalities according an embodiment.

It should be appreciated that various embodiments described herein concerning a liquid analyzer for analyzing fault gases may also be used for other gases, i.e. target gases, gases of interest or analyzed gases. Such gases may be analyzed for various purposes including for example condition monitoring of devices, controlling industrial processes, fault detection in various technical fields of industry. Depending on the target gases and disturbing gases in a particular application of the gas analysis, the temperature dependencies of solubility may be different than described above for analyzing fault gas concentrations. Accordingly, the various embodiments described herein may be applied at least for analyzing target gases in other applications, where a reference fault gas concentration may be determined on the basis of fault gas concentration measurements performed in a temperature, where distortion of the disturbing gases to the target gas concentration measurements is at least relatively low compared to one or more temperatures of the temperature range, where the target gases are analyzed.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

It should be appreciated that various embodiments described herein may be implemented by means that are caused to perform one or more functions described in the embodiments. Suitable means may comprise means known to the skilled person, for example a computer, a processor, a memory device, a computer program that may be combined in various ways to cause one or more functions described in the embodiments. For example, a computer program may be stored on a memory device accessible to computer or a processor for execution of the code.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

Industrial Applicability

The present invention can be used for analysing fault gas concentrations in liquid. The fault gas concentrations can be used in condition monitoring of industrial devices since fault gases are dissolved to the liquid that interacts with devices or one or more components of the devices.

ACRONYMS LIST

H2 Hydrogen
CO Carbon monoxide
CO2 Carbon dioxide
CH4 Methane
C2H2 Acetylene
C2H4 Ethylene
C2H6 Ethane
IEEE Institute of Electrical and Electronics Engineers
DGA Dissolved gas analysis
NDIR Nondispersive infrared
PAS Photoacoustic spectroscopy
S Linearized absorption spectrum or photoacoustic power spectrum
Sf Fault gas contribution to linearized absorption spectrum or photoacoustic power spectrum
Sd Disturbing gas contribution to linearized absorption spectrum or photoacoustic power spectrum
T Temperature
$T_{low}$ Low extraction temperature
Sf,est Estimate of fault gas contribution to linearized absorption spectrum or photoacoustic power spectrum
Sd,est Estimate of disturbing gas contribution to linearized absorption spectrum or photoacoustic power spectrum

REFERENCE SIGNS LIST

100 Liquid analyzer
102 Gas analyzer
103 Cold trap
104 Gas sampling system
106 Controller
108 Memory
202-206 Phases of FIG. 2
302-306 Extrapolation functions
308 Results of the fault gas concentration measurements
310 Temperature range
312 Temperature outside the temperature range
314,315 Fault gas concentration measured at one of the lowest temperature points of the temperature range
316-320 Fault gas concentration extrapolated to a lower temperature outside the temperature range

The invention claimed is:

1. A method for analyzing fault gas concentrations in a liquid obtained from an electrical asset, the method comprising:
    measuring, by a liquid analyzer comprising a system for sampling gas from the liquid and an analyzer for gas sampled by the system, concentration of at least one dissolved fault gas in the liquid at least at two temperatures within a temperature range for gas sampling, wherein in a first temperature of the at least two temperatures solubility of one or more disturbing gases in the liquid is lower than in a second temperature of the at least two temperatures;
    determining, by the liquid analyzer, a disturbing gas contribution in at least one temperature on the basis of the fault gas concentration measurements by utilizing differences in solubility of the fault gas and the disturbing gases; and
    analyzing, by the liquid analyzer, fault gas concentrations by compensating fault gas concentrations on the basis of the determined disturbing gas contribution.

2. The method according to claim 1, further comprising: filtering, prior to measuring concentration of the at least one fault gas, disturbing gases from the sampled gas by a cold trap arranged in the liquid analyzer.

3. The method according to claim 2, wherein the cold trap is operated in one or more filtering temperatures and the disturbing gas contribution is determined on the basis of fault gas concentrations measured from filtered gas samples.

4. The method according to claim 1, further comprising: determining disturbing gas contributions at temperatures outside of the temperature range for gas sampling.

5. The method according to claim 1, further comprising: determining a reference fault gas concentration in the liquid on the basis of
    a fault gas concentration measured at one of the lowest temperature points of the temperature range for gas sampling, or
    a fault gas concentration extrapolated to a lower temperature outside of the temperature range for gas sampling; and
    determining fault gas contribution in the gas measurement at one, two or more temperatures on the basis of the temperature dependence of the solubility of the fault gases and the determined reference fault gas concentration.

6. The method according to claim 1, wherein the disturbing gases comprise heavier hydrocarbons than the fault gases.

7. The method according to claim 1, wherein the fault gases comprise at least one of hydrogen, water, methane, ethane, ethylene, acetylene, carbon monoxide and carbon dioxide.

8. The method according to claim 1, wherein the disturbing gases comprise at least one of light alcohols, ketones and aldehydes, or hydrocarbons containing at least 3 carbon atoms per molecule.

9. The method according to claim 1, wherein at least part of the fault gas measurements are performed in a time interval wherein there is a local minimum in ambient temperature.

10. The method according to claim 1, wherein the measurements at least at two temperatures are performed in a symmetrical and/or cyclical order with respect to temperature to reduce the effects of change in gas concentrations in the liquid during the measurements.

11. The method according to claim 1, wherein the liquid analyzer is a hermetical system.

12. A liquid analyzer comprising a system for sampling gas from a liquid obtained from an electrical asset and an analyzer for gas sampled by the system, wherein the liquid analyzer is configured to:
    measure concentration of at least one dissolved fault gas in the liquid at least at two temperatures within a temperature range for gas sampling, wherein in a first temperature of the at least two temperatures solubility of one or more disturbing gases in the liquid is lower than in a second temperature of the at least two temperatures;
    determine a disturbing gas contribution in at least one temperature on the basis of the fault gas concentration measurements by utilizing differences in solubility of the fault gas and the disturbing gases; and analyze fault gas concentrations by compensating fault gas concentrations on the basis of the determined disturbing gas contribution.

13. The liquid analyzer according to claim 12, wherein the liquid analyzer is caused to perform a method for analyzing fault gas concentrations in a liquid obtained from an electrical asset, the method comprising:
measuring, by a liquid analyzer comprising a system for sampling gas from the liquid and an analyzer for gas sampled by the system, concentration of at least one dissolved fault gas in the liquid at least at two temperatures within a temperature range for gas sampling, wherein in a first temperature of the at least two temperatures solubility of one or more disturbing gases in the liquid is lower than in a second temperature of the at least two temperatures;
determining, by the liquid analyzer, a disturbing gas contribution in at least one temperature on the basis of the fault gas concentration measurements by utilizing differences in solubility of the fault gas and the disturbing gases; and
analyzing, by the liquid analyzer, fault gas concentrations by compensating fault gas concentrations on the basis of the determined disturbing gas contribution.

14. A computer program product comprising instructions to cause a liquid analyzer comprising a system for sampling gas from the liquid and an analyzer for gas sampled by the system, to execute a method for analyzing fault gas concentrations in a liquid obtained from an electrical asset, the method comprising:
measuring, by a liquid analyzer comprising a system for sampling gas from the liquid and an analyzer for gas sampled by the system, concentration of at least one dissolved fault gas in the liquid at least at two temperatures within a temperature range for gas sampling, wherein in a first temperature of the at least two temperatures solubility of one or more disturbing gases in the liquid is lower than in a second temperature of the at least two temperatures;
determining, by the liquid analyzer, a disturbing gas contribution in at least one temperature on the basis of the fault gas concentration measurements by utilizing differences in solubility of the fault gas and the disturbing gases; and
analyzing, by the liquid analyzer, fault gas concentrations by compensating fault gas concentrations on the basis of the determined disturbing gas contribution.

* * * * *